United States Patent
Lim et al.

(10) Patent No.: US 12,168,142 B2
(45) Date of Patent: Dec. 17, 2024

(54) LIGHT OUTPUTTING DEVICE FOR SKIN CARE

(71) Applicant: LG ELECTRONICS INC., Seoul (KR)

(72) Inventors: Gueisam Lim, Seoul (KR); Munseong Kang, Seoul (KR); Sangwon Kim, Seoul (KR); Heejung Kim, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 778 days.

(21) Appl. No.: 17/285,746

(22) PCT Filed: May 13, 2019

(86) PCT No.: PCT/KR2019/005735
§ 371 (c)(1),
(2) Date: Apr. 15, 2021

(87) PCT Pub. No.: WO2020/080631
PCT Pub. Date: Apr. 23, 2020

(65) Prior Publication Data
US 2022/0001196 A1    Jan. 6, 2022

Related U.S. Application Data

(60) Provisional application No. 62/746,565, filed on Oct. 17, 2018.

(30) Foreign Application Priority Data

Apr. 2, 2019  (KR) ........................ 10-2019-0038444

(51) Int. Cl.
*A61N 5/06*    (2006.01)

(52) U.S. Cl.
CPC .... *A61N 5/0616* (2013.01); *A61N 2005/0626* (2013.01); *A61N 2005/0652* (2013.01);
(Continued)

(58) Field of Classification Search
CPC .......... A61N 5/0616; A61N 2005/0626; A61N 2005/0652; A61N 2005/0659;
(Continued)

(56) References Cited

U.S. PATENT DOCUMENTS

| | | | | |
|---|---|---|---|---|
| 2013/0304019 A1* | 11/2013 | Cooper | ................. | A61N 5/062 604/20 |
| 2015/0297913 A1* | 10/2015 | Knaus | ..................... | B32B 27/40 156/60 |
| 2016/0346564 A1* | 12/2016 | Burgmann | ............. | H05B 47/10 |

FOREIGN PATENT DOCUMENTS

| | | |
|---|---|---|
| KR | 10-2011-0138003 A | 12/2011 |
| KR | 10-1324255 B1 | 11/2013 |

(Continued)

OTHER PUBLICATIONS

Degree of curvature. Degree of curvature—GIS Wiki | The GIS Encyclopedia. (n.d.). http://wiki.gis.com/wiki/index.php/Degree_of_curvature (Year: 2023).*

(Continued)

*Primary Examiner* — Paula J Stice
(74) *Attorney, Agent, or Firm* — Birch, Stewart, Kolasch & Birch, LLP

(57) ABSTRACT

According to an embodiment of the present disclosure, a light outputting device for skin care includes a care module including at least one or more care light sources and a care module substrate on which the at least one or more care light sources are mounted; a housing configured to surround the care module; a care body including the care module and the housing; and a length adjustment part connected to both (Continued)

ends of the care body, wherein the housing and the care module substrate are formed to have a first curvature in a first direction and a second curvature in a second direction, and wherein at least one of the first curvature and the second curvature is variable within a predetermined range.

12 Claims, 10 Drawing Sheets

(52) U.S. Cl.
CPC ............... *A61N 2005/0659* (2013.01); *A61N 2005/0663* (2013.01)

(58) Field of Classification Search
CPC .... A61N 2005/0663; A61N 2005/0645; A61N 2005/0662
See application file for complete search history.

(56) References Cited

FOREIGN PATENT DOCUMENTS

| KR | 10-1648415 B1 | 8/2016 |
|----|---------------|--------|
| KR | 10-2018-0021338 A | 3/2018 |
| KR | 10-2018-0038199 A | 4/2018 |

OTHER PUBLICATIONS

Merriam-Webster. (n.d.). Curvature definition & meaning. Merriam-Webster. https://www.merriam-webster.com/dictionary/curvature (Year: 2023).*

* cited by examiner

[Figure 1]
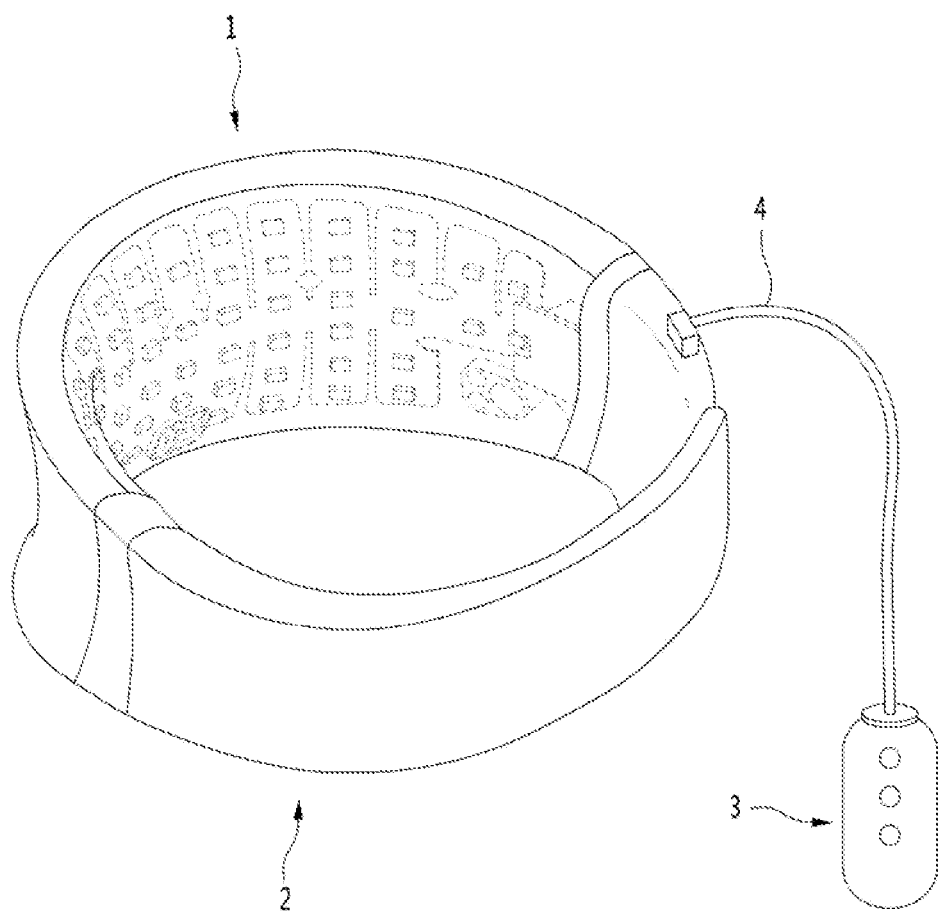

[Figure 2]
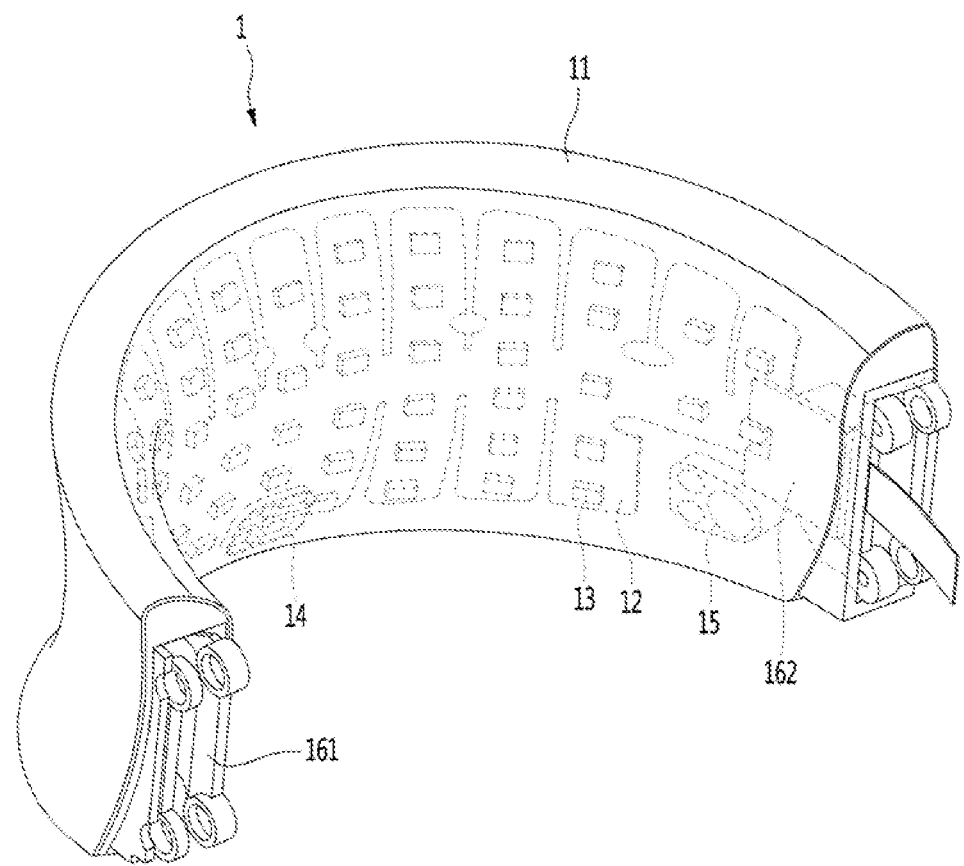

[Figure 3]
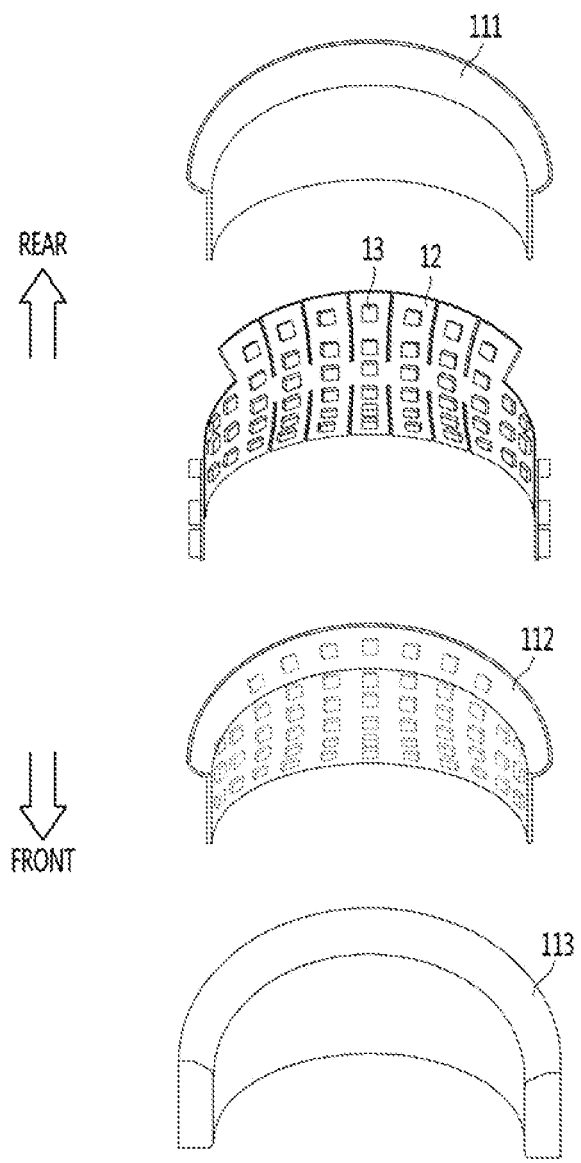

[Figure 4]
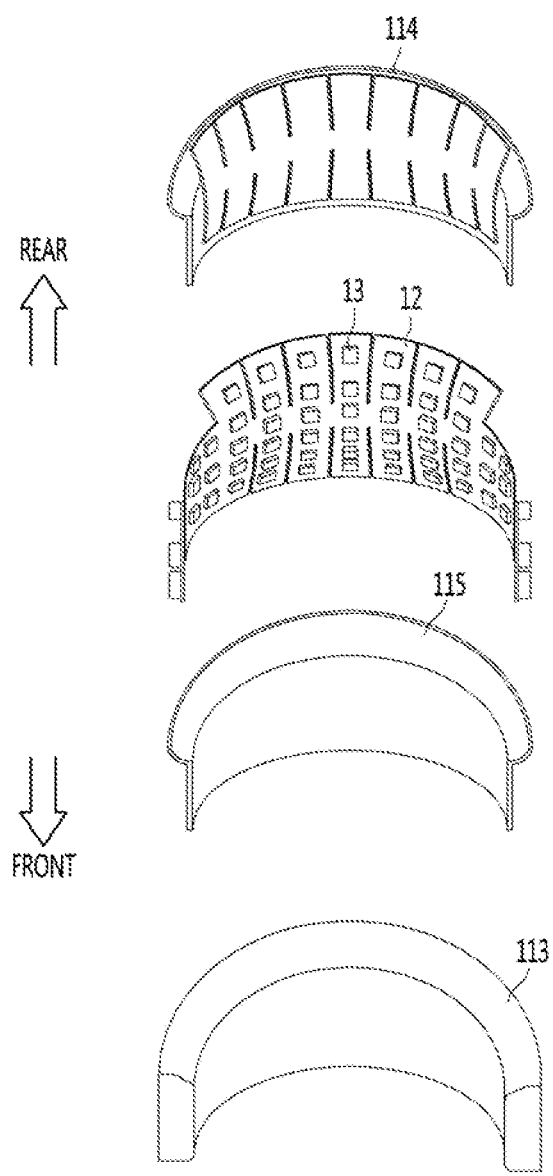

[Figure 5]
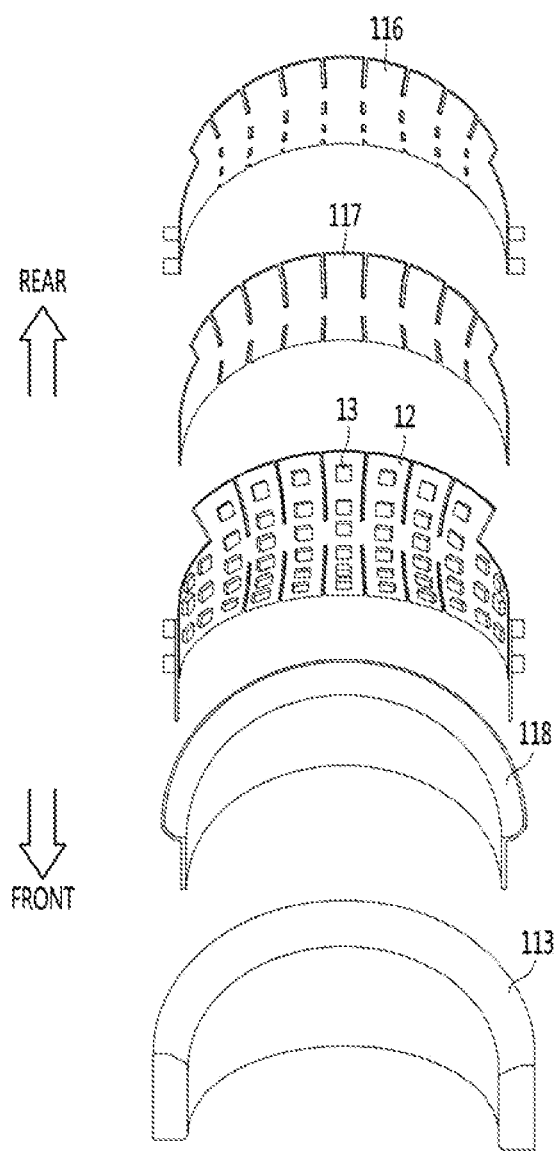

[Figure 6]
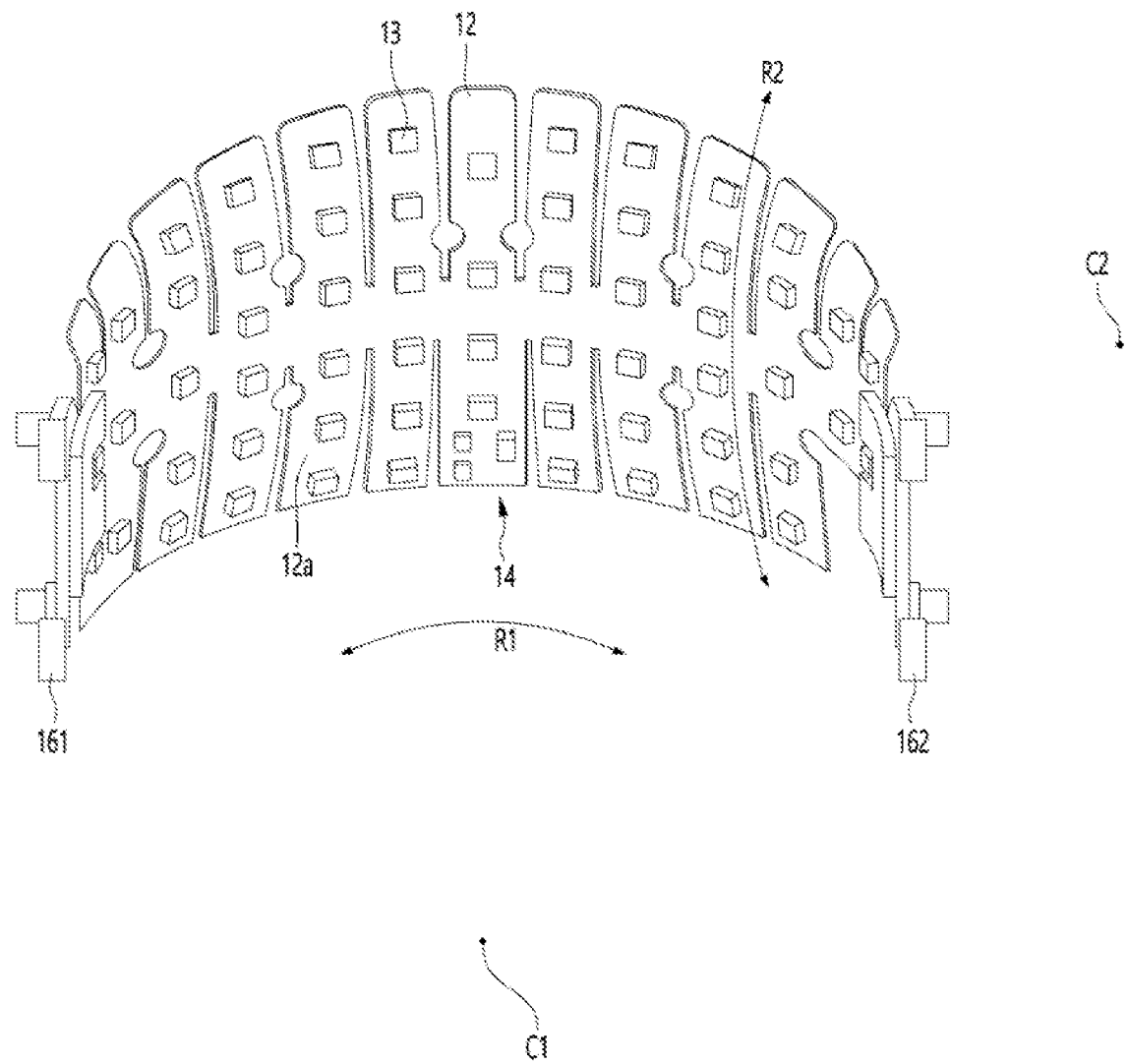

【Figure 7】
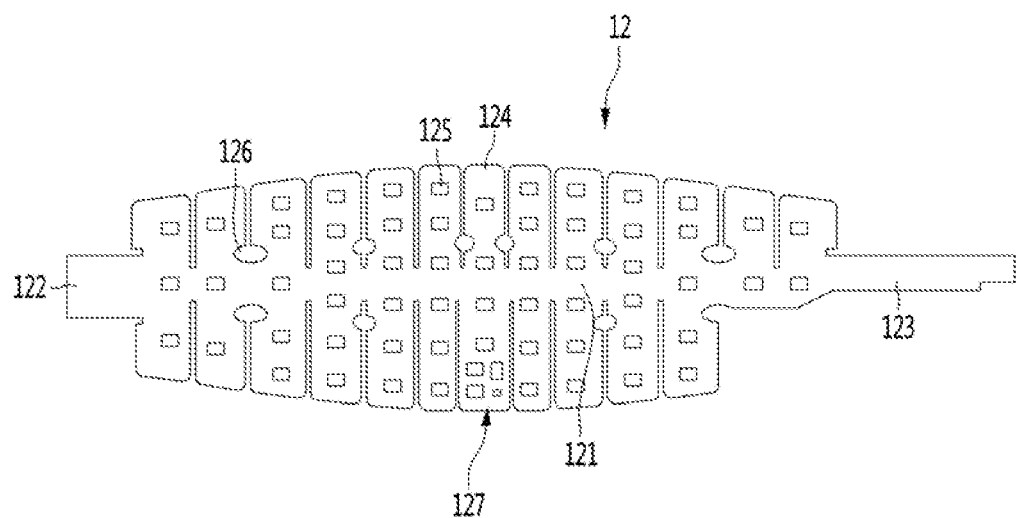
【Figure 8】
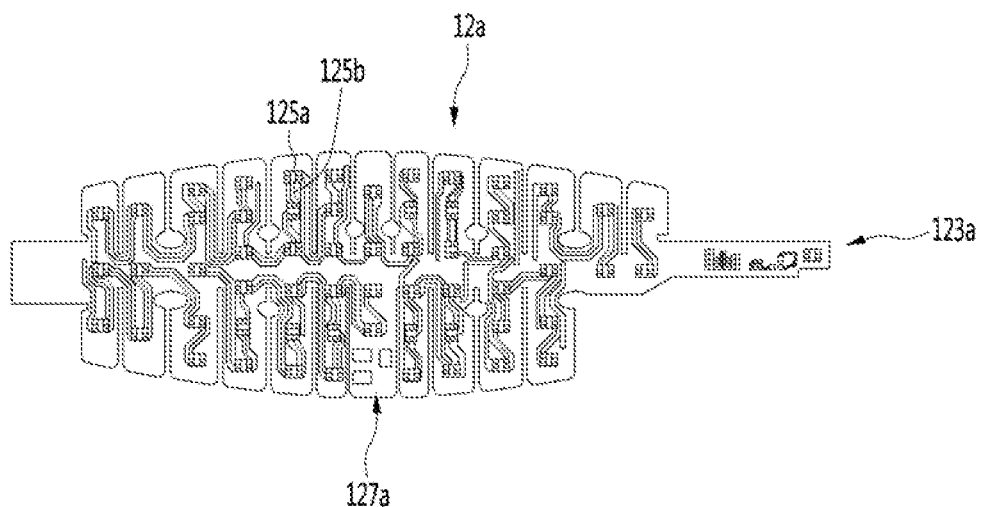

[Figure 9]
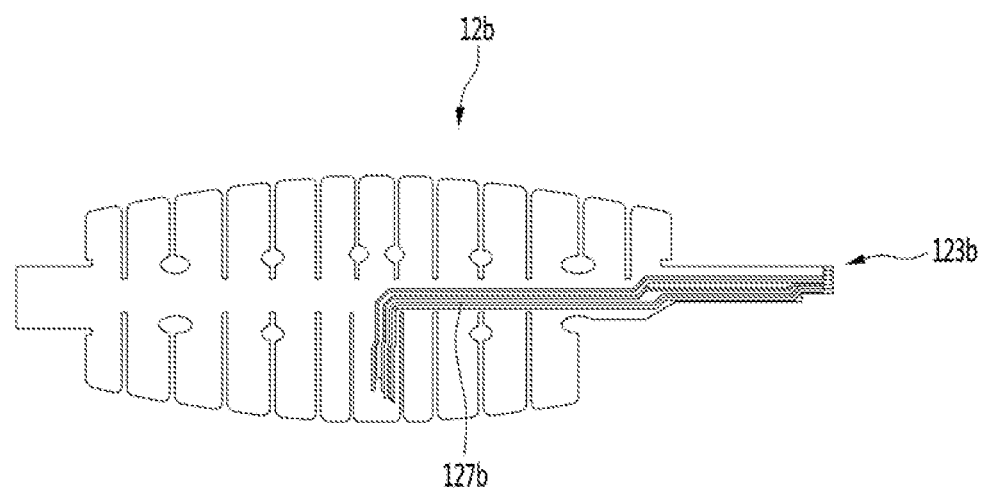

【Figure 10】
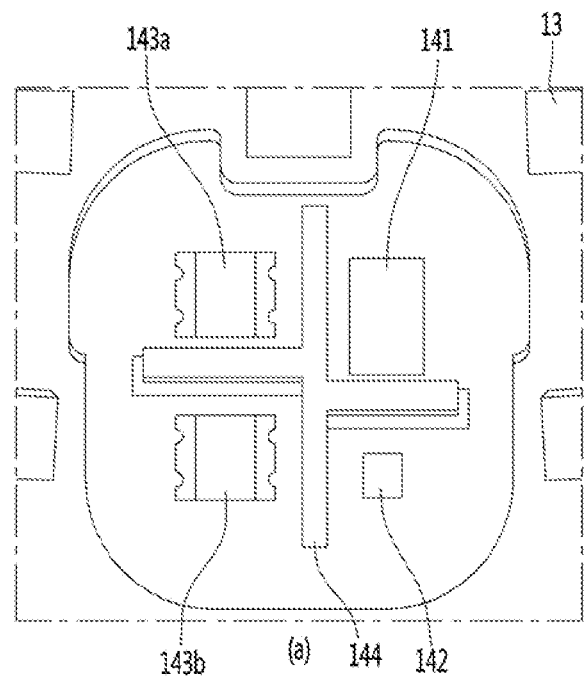
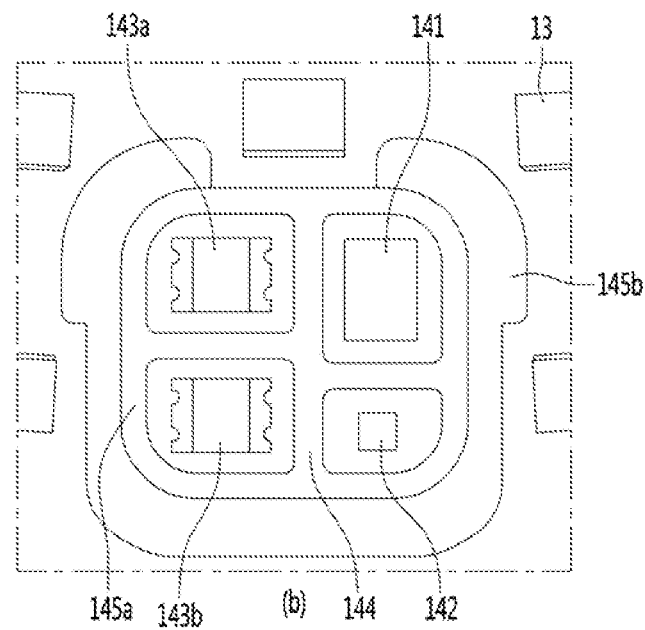

[Figure 11]
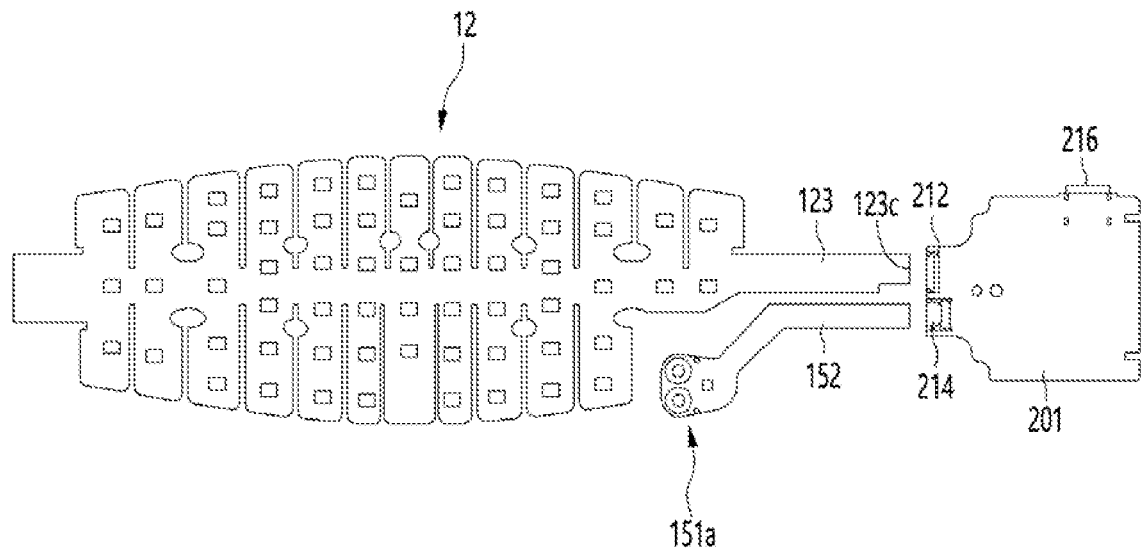
[Figure 12]
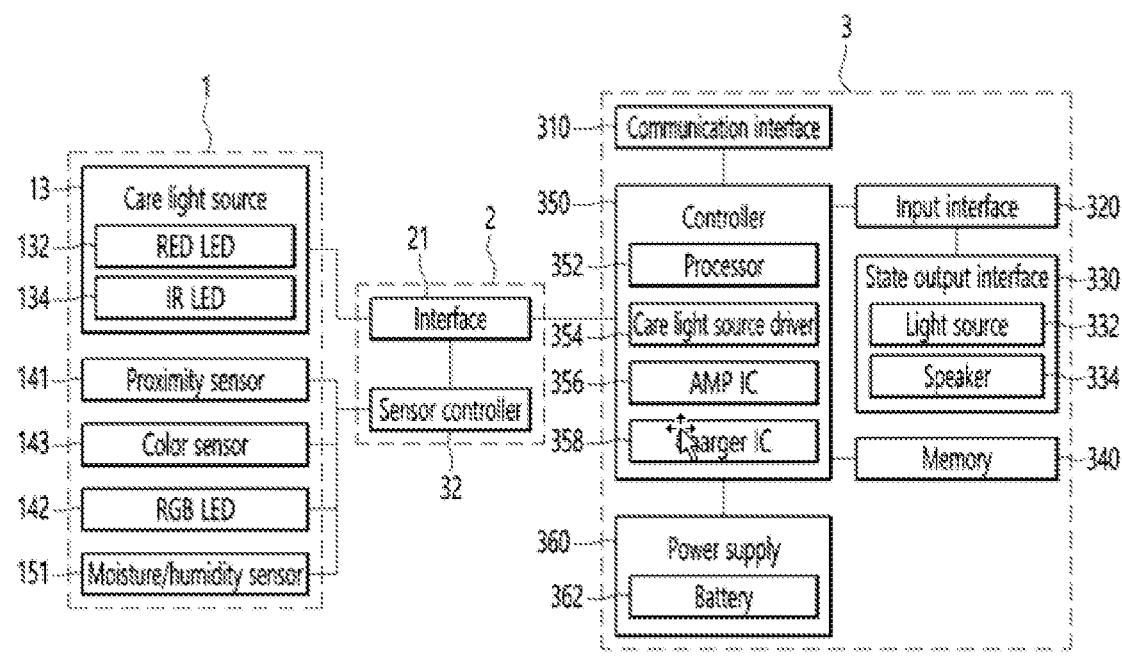

LIGHT OUTPUTTING DEVICE FOR SKIN CARE

CROSS-REFERENCE TO RELATED APPLICATIONS

This application is the National Phase of PCT International Application No. PCT/KR2019/005735 filed on May 13, 2019, which claims priority under 35 U.S.C. § 119(e) to U.S. Provisional Application No. 62/746,565, filed on Oct. 17, 2018, and under 35 U.S.C. § 119(a) to Patent Application No. 10-2019-0038444, filed in Republic of Korea on Apr. 2, 2019, all of these applications are hereby expressly incorporated by reference into the present application.

TECHNICAL FIELD

The present disclosure relates to a skin care device, and more particularly, to a device that is worn on a body part such as a user's neck and outputs light for skin care.

BACKGROUND ART

Skin may be damaged due to aging of cells, repetition of certain facial expressions, constant exposure to external environments (ultraviolet rays, fine dust, or the like), stress, and the like. For example, aging of cells or repetition of specific facial expressions may cause wrinkles in the skin, and continuous exposure to external environments or stress may cause various troubles such as acne and freckle.

Skin care for preventing or minimizing such damage to the skin aims to maintain clean and soft skin by removing blemishes, and particularly, the most attention has been formed on the skin care for the face among body parts. Therefore, people try to receive a massage, apply functional cosmetic products, or keep their skin clean by using various cleaning products for facial skin care.

In particular, recently, devices that output light when being attached or worn on various parts such as a user's face have appeared. In such a light outputting device includes a plurality of light sources (e.g., LEDs) arranged to output light toward the user's facial skin or neck skin.

On the other hand, the light outputting device needs to be implemented to provide a uniform light output function or an optimal fit even if the body characteristics such as users' neck thicknesses and lengths are different from each other.

DISCLOSURE

Technical Problem

An object of the present disclosure is to provide a light outputting device for skin care capable of performing skin care for various locations of a user's neck.

Another object of the present disclosure is to provide a light outputting device for skin care capable of providing a uniform light output function and an optimal fit by reflecting characteristics such as the thickness or length of a user's neck.

Technical Solution

According to an embodiment of the present disclosure, a light outputting device for skin care includes a care module including at least one or more care light sources and a care module substrate on which the at least one or more care light sources are mounted; a housing configured to surround the care module; a care body including the care module and the housing; and a length adjustment part connected to both ends of the care body, wherein the housing and the care module substrate are formed to have a first curvature in a first direction and a second curvature in a second direction, and at least one of the first curvature and the second curvature is variable within a predetermined range.

The center of curvature of the first curvature and the center of curvature of the second curvature may be located in opposite directions from each other with respect to the care module.

The at least one or more care light sources may be mounted on a surface facing the center of curvature of the first curvature among both surfaces of the care module substrate.

The care module substrate may include a substrate body formed in the first direction; and a plurality of branch substrates extending in the second direction respectively from a plurality of positions in the substrate body, and the plurality of branch substrates may be spaced apart from each other by a predetermined distance in the first direction.

The at least one or more care light sources may be mounted to be spaced apart from each other on one-side surfaces of the substrate body and the plurality of branch substrates.

The plurality of branch substrates include a first branch substrate formed at a first position of the substrate body, and a second branch substrate formed at a second location where a distance from a center of the substrate body is farther than that at the first location, and a length of the first branch substrate may be longer than a length of the second branch substrate.

The housing may be formed by including silicon, and the care module substrate may be formed by including at least one of polyimide (PI), polyester (PET), and glass epoxy (GE).

The housing may include a transparent or opaque first inner housing formed on a surface facing the center of curvature of the second curvature among both surfaces of the care module, a transparent second inner housing formed on a surface facing the center of curvature of the first curvature among both surfaces of the care module, and an outer housing formed to surround the first inner housing and the second inner housing.

The first inner housing may be formed of stainless use steel (SUS) material, and a double sided adhesive (DSA) layer may be provided between the first inner housing and the care module to bond the first inner housing and the care module.

Each of the at least one care light source may include an RED LED configured to emit red light; and an IR LED configured to emit infrared light.

The care body may further include a first sensor part including a proximity sensor for detecting whether or not wearing is made, and a color sensor for obtaining skin color information of a user, and a second sensor part including a moisture/humidity sensor for detecting a user's skin condition.

The first sensor part may be formed on the care module substrate, and the second sensor part may be formed on a sensor substrate spaced apart from the care module substrate.

According to an embodiment, a first circuit corresponding to the at least one care light source and a second circuit corresponding to the first sensor part may be formed on the care module substrate, and the first circuit and the second circuit may be formed on different surfaces of the care module substrate.

According to an embodiment, a partition wall having a predetermined height from the care module substrate may be formed between the first sensor part and the at least one care light source.

The light outputting device may further include an interface module provided inside the length adjustment part, and a user operation device connected to the interface module, and the care module substrate may have a terminal formed at one end thereof and coupled to a slot of the interface module.

The user operation device may include a controller configured to control on/off of the at least one care light source, and a battery configured to supply power to the care module.

Advantageous Effects

According to an embodiment of the present disclosure, the care body of the light outputting device for skin care is implemented such that the curvature thereof is changed according to the characteristics of the user's body part on which the light outputting device is worn, thereby providing an optimal fit for various users and uniform light and providing skin care effect according to uniform light output.

In addition, the care module substrate included in the care body is formed such that not only the curvature in the horizontal direction but also the curvature in the vertical direction are variable, so that the care body can be deformed by reflecting the neck thickness and the neck length individually, when worn on the user's neck. Accordingly, a sense of stability when worn by the user can be maximized.

In addition, since a partition wall is formed between the first sensor part and the care light source on the care module substrate, it is possible to prevent a problem in that the sensing accuracy of the first sensor part decreases due to light emitted from the care light source.

In addition, the light output device for skin care includes a user operation device implemented in a separate configuration from the care body, so that the user can conveniently operate the light outputting device by using the user operation device even while wearing the light outputting device for skin care.

In addition, since the battery of the light outputting device for skin care is provided in the user operation device, the weight of the care body and the length adjustment part is minimized, so that discomfort due to weight during wearing may be reduced.

DESCRIPTION OF DRAWINGS

FIG. 1 is a perspective view of a light outputting device for skin care according to an embodiment of the present disclosure.

FIG. 2 is a perspective view of a care body of a light outputting device for skin care according to an embodiment of the present disclosure.

FIGS. 3 to 5 are exploded perspective views showing various implementation examples of the care body shown in FIG. 2.

FIG. 6 is a diagram showing a care module substrate included in the care body shown in FIG. 2.

FIG. 7 is an exploded view showing a front surface of the care module substrate shown in FIG. 6.

FIG. 8 is an exemplary diagram of a circuit formed on one surface of the care module substrate shown in FIG. 6.

FIG. 9 is an exemplary diagram of a circuit formed on the other surface of the care module substrate shown in FIG. 8.

FIG. 10 is an enlarged view of a first sensor part provided in the care module.

FIG. 11 is a diagram showing a care module and a moisture/humidity sensor module provided in a care body, and an interface module provided in a length adjustment part.

FIG. 12 is a block diagram illustrating a control configuration of an light outputting device for skincare according to an embodiment of the present disclosure.

MODE FOR INVENTION

Hereinafter, the embodiments disclosed herein will be described in detail with reference to the accompanying drawings, and the same or similar elements are designated with the same numeral references regardless of the numerals in the drawings and their redundant description will be omitted. The suffixes "module" and "unit or portion" for components used in the following description are merely provided only for facilitation of preparing this specification, and thus they are not granted a specific meaning or function. In addition, when it is determined that the detailed description of the related known technology may obscure the gist of embodiments disclosed herein in describing the embodiments, a detailed description thereof will be omitted. Further, the accompanying drawings are intended to facilitate understanding of the embodiments disclosed herein, and the technical spirit disclosed herein are not limited by the accompanying drawings. Therefore, the present disclosure should be construed as including all the changes, equivalents, and substitutions included in the spirit and scope of the present disclosure.

The terms coming with ordinal numbers such as 'first', 'second', or the like may be used to denote various components, but the components are not limited by the terms. The terms are used merely for the purpose to distinguish a component from the other component.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

As used herein, singular forms may include plural forms as well unless the context clearly indicates otherwise.

It will be further understood that the terms "comprises," "comprising," "having," "having," "includes," "including" and/or variations thereof, when used in this specification, specify the presence of stated features, integers, steps, operations, elements, and/or components, but do not preclude the presence or addition of one or more other features, integers, steps, operations, elements, components, and/or groups thereof.

Hereinafter, embodiments of the present disclosure will be described in detail with reference to the accompanying drawings.

FIG. 1 is a perspective view of a light outputting device for skin care according to an embodiment of the present disclosure.

Referring to FIG. 1, a light outputting device for skin care (hereinafter referred to as 'light outputting device') according to an embodiment of the present disclosure may be a device that stimulates the activity of skin cells by outputting light to a user's skin to achieve improvements in skin elasticity and wrinkles, skin tone, or the like or to help solve skin problems when is worn on the user's body (e.g., neck).

The light outputting device may include a care body 1 and a length adjustment part 2 fastened to both ends of the care body 1.

Hereinafter, for convenience of description, it is assumed that the light outputting device is worn on the user's neck, but the light outputting device may be worn on the user's other body parts such as arms or legs.

The care body 1 may be worn on the user's neck to output light to the user's skin. To this end, at least one light source (a care light source 13) may be provided in the care body 1.

In addition, the care body 1 may include various sensors, such as, a sensor for measuring the user's skin condition (e.g., moisture content), a sensor for detecting a user's skin characteristics (e.g., skin tone), a sensor for detecting whether or not the light outputting device is worn, and/or the like.

Meanwhile, the care body 1 may have a length in the horizontal direction longer than the length in the vertical direction so as to surround at least a portion of a person's neck when worn. In addition, the care body 1 may be formed to be rounded along the shape of a person's neck in order to evenly apply light to the user's neck.

In addition, since the care body 1 is made of soft materials, at least one of a horizontal curvature and a vertical curvature may vary within a predetermined range according to various neck thicknesses or lengths of users. Accordingly, the light outputting device may provide an optimal fit for each of various users, and may provide uniform light output. Embodiments related to the care body 1 will be described in more detail later with reference to FIGS. 2 to 10.

The length adjustment part 2 may be fastened to both ends of the care body 1 in the horizontal direction, respectively. For example, the length adjustment part 2 may include two bands separated/coupled to/from each other in a predetermined area. The two bands may be fastened to different ends of the care body 1. That is, the care body 1 and the length adjustment part 2 may form a band-shaped appearance.

When the two bands are coupled to each other, an overlapping area may occur, and the size of the overlapping area may be adjusted. As the overlapping area increases, the circumference of the care body 1 and the length adjustment part 2 may decrease. On the other hand, as the overlapping area decreases, the circumference of the care body 1 and the length adjustment part 2 may increase. That is, the size of the light outputting device may be adjusted by the length adjustment part 2.

In addition, the curvature of the care body 1 in the horizontal direction may be adjusted by the length adjustment part 2. As the overlapping area between the two bands increases, the curvature of the care body 1 in the horizontal direction may increase. On the other hand, as the overlapping area between the two bands decreases, the curvature of the care body 1 in the horizontal direction may decrease.

According to an embodiment, an interface module 21 (see FIG. 12) and a sensor controller 32 (see FIG. 12) may be provided inside one of the two bands of the length adjustment part 2.

The interface module 21 provides an interface between a user operation device 3 to be described later and a care module in the care body 1, so that a controller 350 in the user operation device 3 (see FIG. 12) may control driving of the care light source 13 included in the care module or the like.

The sensor controller 32 may control the operation of at least one sensor provided in the care body 1.

The light outputting device may further include a user operation device 3. For example, the user operation device 3 may be wiredly connected to the interface module 21 in the length adjustment part 2 through a cable 4, a cable 52, and the like, but this is not necessary, and may be wirelessly connected through a wireless communication method. In this case, a wireless communication chip or element supporting wireless communication may be further provided on a sub-board 201 of the length adjustment part 2.

For example, the user operation device 5 may be formed in a cylindrical shape so that the user can easily hold and use it with his or her hand. The user operation device 3 may be provided with at least one button as an input interface for operating the light outputting device.

The user operation device 3 may provide an interface for turning on/off the power of the light outputting device or setting an operation mode of the light outputting device for use by the user. As the user operation device 3 is implemented as a separate configuration from the care body 1, the user may conveniently operate an operation of the light outputting device by using the user operation device 3 while wearing the care body 1.

In addition, the user operation device 3 may be provided with a battery that provides power for the operation of the light outputting device. As the battery is provided in the user operation device 3, the weight of the light outputting device can be minimized to minimize user's inconvenience when the user wears the light outputting device.

Control components included in the user operation device 3 will be described later with reference to FIG. 12.

FIG. 2 is a perspective view of a care body of a light outputting device for skin care according to an embodiment of the present disclosure. FIGS. 3 to 5 are exploded perspective views showing various implementation examples of the care body shown in FIG. 2.

Referring to FIG. 2, the care body 1 may include a housing 11, a care module substrate 12 on which a care module is formed, a care light source 13, a first sensor part 14, and a second sensor part 15, and inner frames 161 and 162.

The housing 11 may define the overall appearance of the care body 1. For example, the housing 11 may be formed of a soft material such as silicon or stainless use steel (SUS) and bend to have a predetermined curvature.

For example, the curvature of the housing 11 may be changed by a length adjustment part 2. When the user wears the light outputting device, the user may adjust a length of the length adjustment part 2 based on the length of the user's neck circumference. As the length of the length adjustment part 2 is adjusted, the curvature of the housing 11 in the horizontal direction may be changed. For example, the curvature of the housing 11 in the horizontal direction may decrease as the length of the circumference of the user's neck increases.

In addition, the housing 11 may have a variable curvature in a vertical direction, the curvature varying according to the length of the user's neck. When the light outputting device is worn on the user's neck, the upper end of the housing 11 may contact the lower chin (or upper portion of the neck) of the user, and the lower end of the housing 11 may contact the lower neck of the user. Accordingly, since the housing 11 receives pressure in the vertical direction, the curvature in the vertical direction may be changed due to the pressure.

Hereinafter, when both surfaces of the care body 1 are defined, a surface facing the user's skin when worn is defined as the front surface, and the opposite side is defined as the back surface.

Accordingly, the front surface of the housing 11 may be formed to be transparent. For example, the front surface may be formed of transparent silicon. Accordingly, light emitted from the care light source 13 of the care module accommodated in the housing 11 may pass through the front surface of the housing 11 and be applied to the user's skin.

The housing 11 may define an accommodation space for accommodating the care module therein. The care module may be implemented such that at least one care light source 13 is mounted on the care module substrate 12. For example, the care module substrate 12 may be implemented with a flexible printed circuit board (FPCB). The FPCB may include materials such as PI (polyimide), PET (polyester), and GE (glass epoxy).

Since the care module substrate 12 is implemented with the FPCB, the care module may be formed to be round to correspond to the shape of the housing 11. In addition, the care module substrate 12 may have a variable curvature that varies to correspond to a change in curvature of the housing 11.

The care module substrate 12 may have a shape to be rounded in a horizontal direction and a vertical direction, respectively. Details related to the shape of the care module substrate 12 will be described later with reference to FIGS. 6 to 7.

Meanwhile, the housing 11 may be implemented in various ways to accommodate the care module therein. Hereinafter, implementation examples of the housing 11 will be described with reference to FIGS. 3 to 5.

Referring to FIGS. 3 to 5, the housing 11 may be implemented with a type of double injection structure including at least one inner housing and an outer housing surrounding the at least one inner housing.

Referring to FIG. 3, the housing 11 may include a first inner housing 111 formed on the rear surface of the care module substrate 12, and a second inner housing 112 formed on the front surface of the care module substrate 12. For example, the first inner housing 111 and the second inner housing 112 may be made of a transparent silicon.

The first inner housing 111 and the second inner housing 112 may be bonded to each other in the edge region by thermal bonding or the like, and the care module is disposed between the first inner housing 111 and the second inner housing 112. As the second inner housing 112 is made of a transparent silicon, the care light source 13 mounted on the care module substrate 12 may apply light to the front surface of the light outputting device through the second inner housing 112.

On the other hand, when the curvature of the housing 11 is changed due to a force applied when adjusting the length of the length adjustment part 2 or the other external force, the curvature of the care module substrate 12 may be also changed correspondingly. In this case, in order to guide a stable change in curvature of the care module substrate 12, the rear surface of the second inner housing 112 may be formed to correspond to the front surface of the care module substrate 12.

Accordingly, when the first inner housing 111 is bonded to the second inner housing 112, the rear surface of the second inner housing 112 may be in close contact with the front surface of the care module substrate 12.

According to the embodiment of FIG. 3, when a force for adjusting the length of the length adjustment part 2 or an external force is applied, the curvatures of the first inner housing 111 and the second inner housing 112 may be changed. In addition, as the curvature of the second inner housing 112 is changed, the curvature of the care module substrate 12 in close contact with the second inner housing 112 may be also changed.

On the other hand, referring to FIG. 4, unlike the embodiment of FIG. 3, the front surface of the first inner housing 114 may be formed to correspond to the rear surface of the care module substrate 12. In this case, when the first inner housing 114 is bonded to the second inner housing 115, the front surface of the first inner housing 114 may be in close contact with the rear surface of the care module substrate 12.

According to the embodiment of FIG. 4, when a force for adjusting the length of the length adjustment part 2 or an external force is applied, the curvatures of the first inner housing 114 and the second inner housing 115 may be changed. In addition, as the curvature of the first inner housing 114 is changed, the curvature of the care module substrate 12 in close contact with the first inner housing 114 may be also changed.

Meanwhile, referring to FIG. 5, the first inner housing 116 may be formed of a plate made of stainless use steel (SUS). Since light is not emitted through the rear surface of the light outputting device, the function of the light outputting device may be normally provided even if the first inner housing 116 is formed of opaque SUS.

The first inner housing 114 may be adhered to the care module substrate 12 through a double side adhesive (DSA) 117. The first inner housing 114 and the DSA 117 are formed to correspond to the rear surface of the care module substrate 12 to guide the change in curvature of the care module substrate 12, like the first inner housing 114 of FIG. 4.

In addition, the second inner housing 118 is formed to be transparent on the front surface of the care module substrate 12 so that light emitted from the care light source 13 is applied to the front surface of the light outputting device.

Meanwhile, referring to FIGS. 3 to 5, the housing 11 may include an outer housing 113 formed to surround a first inner housing and a second inner housing.

In the case of the outer housing 113, the transparency of the rear surface may be different from that of the front surface. For example, the front surface of the outer housing 113 may be transparent to transmit the light of the care light source 13 (or the transparency thereof is greater than or equal to a reference). On the other hand, the rear surface of the outer housing 113 may be opaque such that the care module substrate 12 is not visually exposed. That is, the transparency of the front surface of the outer housing 113 may be higher than the transparency of the rear surface.

However, in some embodiments, both the front and rear surfaces of the outer housing 113 may be transparent.

Meanwhile, the outer housing 113 is formed with the front surface and the rear surface separated, and the front surface and the rear surface are thermally bonded to accommodate the care module and the inner housing therein, thereby forming the care body 1.

Alternatively, an insertion groove into which the care module and the inner housing are inserted may be formed at the upper or lower side of the outer housing 113. Specifically, the care module and the inner housing are inserted into the outer housing 113 through the insertion groove, and then the insertion groove is closed by heat or the like, thus forming the care body 1.

That is, the care body 1 includes the housing 11 surrounding the care module, so that the components included in the care module (the care module substrate 12, the care light source 13, the sensor parts 14 and 15) may be protected from external shock, moisture, or the like.

In addition, the housing 11 includes an inner housing that guides the change of the curvature of the care module substrate 12, enabling stable change of the curvature of the care module substrate 12 when the curvature of the care body 1 is changed due to external force or the like.

Referring back to FIG. 2, at least one or more care light sources 13 may be mounted on the substrate of the care module 12 to be spaced apart from each other. For example, each of the at least one or more care light sources 13 may include a RED LED that emits red light and an IR LED that emits infrared light.

The RED LED may emit red light having a wavelength of about 630 nm to 670 nm. Red light stimulates the activity of skin cells and may be effective in improvements in wrinkles, elasticity, and skin tone. The IR LED may emit infrared light of about 780 nm to 1 mm wavelength (precisely about 850 nm). The infrared light provides heat to the user's skin, thereby maximizing a skin improvement effect by the RED LED, and providing additional effects such as relieving fatigue through muscle relaxation.

On the other hand, in general, wrinkles and skin problems of the neck occur more on the front side than on the back side of the neck. Accordingly, when the light outputting device is worn, the care body 1 may be positioned to correspond to the front of the neck, and the care light source 13 may be arranged to face the front of the neck. Accordingly, the light outputting device may effectively achieve in improvements in wrinkles, elasticity, and skin tone on the front of the neck.

Although not shown, the care light source may also be provided in the length adjustment part 2. For example, the care light source may be disposed on the length adjustment part 2 to face the back of the neck when worn. Accordingly, the light outputting device may also provide a skin care function corresponding to the back of the neck.

The first sensor part 14 may be mounted at a position of the substrate of the care module 12. Like the care light source 13, the first sensor part 14 may be disposed to face the front side.

For example, the first sensor part 14 may include a proximity sensor 141 (see FIG. 10) and color sensors 143*a* and 143*b* (see FIG. 10).

As the light outputting device is worn by a user, the proximity sensor 141 may detect the proximity of a part of the user's body (e.g., a neck) and transmit a detection signal based on the detection result to the user operation device 3. A processor 352 (see FIG. 12) included in the user operation device 3 may recognize the wearing of the light outputting device based on the detection signal and control a care light source driver 354 (see FIG. 12) to enable the care light source 13.

The color sensors 143*a* and 143*b* (comprehensively referred to as 143) may obtain skin color information of a user wearing the light outputting device. For example, the color sensor 143 may include a photodiode (PD) to obtain skin color information of the user. Meanwhile, in order for the color sensor 143 to effectively obtain the skin color information of the user, the first sensor part 14 may include an RGB LED 142 (see FIG. 10) that is turned on when the color sensor 143 is operated. The RGB LED 142 outputs white light when the color sensor 143 is operated, so that a photodiode included in the color sensor 143 may more accurately obtain the skin color information.

The controller 350 may detect the user's skin color based on the skin color information, and control a driving time or brightness of the care light source 13 differently according to the detected skin color.

The second sensor part 15 may be implemented on a separate substrate separated from the substrate of the care module 12 and accommodated in the housing 11. It should be noted that, in some embodiments, the second sensor part 15 may also be implemented on the substrate of the care module 12.

The second sensor part 15 may include a sensor for measuring a user's skin condition. For example, the second sensor part 15 may include a moisture/humidity sensor 151 (see FIG. 12) for measuring a moisture state of the user's skin.

The moisture/humidity sensor 151 may sense a moisture state of the user's skin and provide a sensing value to the controller 350. The controller 350 may detect the user's skin condition based on the sensing value, and control a driving time or brightness of the care light source 13 according to the detected skin condition.

The inner frames 161 and 162 may be coupled to both ends of the substrate included in the care module 12 to support the substrate. In addition, partial regions of the inner frames 161 and 162 are fastened to the inside of the housing 11 and are coupled to the substrate, so that it is possible to effectively prevent the substrate from being dislodged or twisted when the curvature of the housing 11 is changed.

Meanwhile, the remaining partial regions of the inner frames 161 and 162 may be exposed to the outside through both ends of the housing 11. The exposed remaining partial regions may function as a fastening portion to which the length adjustment part 2 is fastened. For example, the fastening portion may include at least one fastening ring, but the fastening portion may be implemented in various ways.

In addition, one of both ends of the substrate of the care module 12 may pass through the inner frame (e.g., 162) and extend to the outside. The extending one end is connected to a sub-substrate 201 (see FIG. 11) in the length adjustment part 2, and accordingly, the care light source 13 and the first sensor part 14 of the care module 12 are connected to the interface module 21 and the sensor controller 32.

Hereinafter, the care module 12 will be described in more detail with reference to FIGS. 6 to 10.

FIG. 6 is a diagram showing a care module substrate included in the care body shown in FIG. 2. FIG. 7 is an exploded view showing a front surface of the care module substrate shown in FIG. 6. FIG. 8 is an exemplary diagram of a circuit formed on one surface of the care module substrate shown in FIG. 6. FIG. 9 is an exemplary diagram of a circuit formed on the other surface of the care module substrate shown in FIG. 8.

Referring to FIG. 6, as described above, at least one or more care light sources 13 and a first sensor part 14 may be mounted on the care module substrate 12.

At least one or more care light sources 13 are mounted on the care module substrate 12 to be spaced apart from each other, so that light can be applied to a large area of the user's body part.

The first sensor part 14 may be disposed on a lower portion of the center of the care module substrate 12, but the arrangement position of the first sensor part 14 may be variously changed.

On the other hand, the color sensor 143 included in the first sensor part 14 is difficult to accurately detect the user's skin tone when red light emitted from the care light source 13 or external light is reflected by the skin and collected. Accordingly, a structure for preventing light from the care light source 13 or external light from being applied to the color sensor 143 may be formed around or outside the first sensor part 14. Details will be described with reference to FIG. 10.

Meanwhile, the care module substrate 12 may be implemented in the housing 11 to have a first curvature R1 in a horizontal direction and a second curvature R2 in a vertical direction. The first curvature R1 and the second curvature R2 may be changed based on a force applied when the length is adjusted by the length adjustment part 2 or a force applied due to contact with the user's body when worn by the user. That is, the care body 1 and the care module substrate 12 may be deformed to suit the physical characteristics of the user.

Specifically, since a human neck has a shape similar to a cylinder, both ends of the care module substrate 12 in the horizontal direction may be located in front of the center. That is, the center C1 of curvature of the care module substrate 12 in the horizontal direction may be located in front of the care module substrate 12.

On the other hand, since the human neck has a shape similar to a concave cylinder when viewed in the horizontal direction, the care module substrate 12 may have both ends in the vertical direction positioned behind the center. That is, the center of curvature C2 of the care module substrate in the vertical direction may be located behind the care module substrate 12.

That is, in the care module substrate 12, the center C1 of curvature in the horizontal direction and the center C2 of curvature in the vertical direction may be located in opposite directions with respect to the care module substrate 12. In this case, it is not easy to implement the curvatures R1 and R2 of the care module substrate 12 with a general substrate.

In this regard, referring to FIG. 7, the care module substrate 12 may be in a flat state when circuits are formed and devices (LEDs, sensors, or the like) are mounted.

The care module substrate 12 may include a substrate body 121 forming a central portion of the care module substrate 12 and having a predetermined length in the horizontal direction.

The substrate body 121 is formed to be elongated in the horizontal direction to guide a change in the curvature of the care module substrate 12 in the horizontal direction.

The care module substrate 12 may include substrate fastening portions 122 and 123 respectively extending from both ends of the substrate body 121 and fastened to the inner frames 161 and 162, respectively. For example, the first substrate fastening portion 122 may be fastened to the first inner frame 161, and the second substrate fastening portion 123 may be fastened to the second inner frame 162.

The second substrate fastening portion 123 may be formed longer than the first substrate fastening portion 122. Accordingly, the end of the second substrate fastening portion 123 is located outside the second inner frame 162 and may be connected to the sub-board 201 of the length adjustment part 2.

Referring to FIG. 7 again, the care module substrate 12 may include a plurality of branch substrates 124 extending vertically (in an upward or downward direction) at a plurality of positions of the substrate body 121.

Each of the plurality of branch substrates 124 may be formed to be spaced apart from each other by a predetermined interval in a horizontal direction, and may be deformed to have a predetermined curvature in a vertical direction. In particular, since the branch substrates 124 are spaced apart from each other, even when the care module substrate 12 is deformed to have a curvature in the horizontal direction, the curvature in the vertical direction may be changed smoothly without influence or interference with the other branch substrates 124. Accordingly, the care module substrate 12 may be deformed such that the center of curvature in the horizontal direction and the center of curvature in the vertical direction are formed in different directions.

According to an embodiment, the branch substrate may not be formed in a partial area of the substrate body 121 in order to secure a space for arranging the moisture/humidity sensor module.

According to an embodiment, a plurality of coupling guide holes 126 may be formed in the care module substrate 12. The care module substrate 12 may be coupled to the housing 11 while being stably fixed to a coupling device (not shown) through the coupling guide holes 126. Accordingly, it is possible to prevent the occurrence of manufacturing defects of the care body 1 due to the movement or twisting of the care module substrate 12 when being coupled thereto the housing 11.

Meanwhile, a plurality of care light source mounting points 125 to which the plurality of care light sources 13 are mounted may be formed on the substrate body 121 and the branch substrates 124. The plurality of care light source mounting points 125 may be formed to be dispersed from each other on the substrate body 121 and the branch substrates 124.

Among the branch substrates 124, the length of the branch substrate formed at the center of the care module substrate 12 may be longer than the length of the branch substrate formed at the edges of the care module substrate 12. In addition, the number of care light source mounting points formed in the center of the care module substrate 12 may be greater than the number of care light source mounting points formed at the edges of the care module substrate 12. Accordingly, the number of the care light sources 13 facing a front portion of the neck that is more frequently exposed to the outside is increased, thereby providing a more intensive skin care function for the front portion of the neck.

Meanwhile, a first sensor part mounting region 127 on which the first sensor part 127 is mounted may be formed on any one of the plurality of branch substrates 124. For example, the first sensor part mounting region 127 may be formed to be adjacent to an end of the branch substrate. In this regard, when the optical outputting device is mounted, the upper and lower ends of the optical outputting device contact the lower chin and the lower neck of the user, and therefore, a change in curvature in the vertical direction may occur. In this case, a region corresponding to the end of the branch substrate may be in closer contact with the user's skin than a region corresponding to the substrate body 121. Accordingly, since the first sensor part 14 is formed to be adjacent to the end of the branch substrate, the sensing accuracy of the first sensor part 14 may be improved.

Referring to FIGS. 8 and 9, a circuit for transmitting power or transmitting and receiving signals to and from the plurality of care light sources 13 and the first sensor part 14 may be configured on the care module substrate 12.

Meanwhile, the care light source 13 and the first sensor part 14 needs to be provided with different power lines and signal transmission lines. However, due to the area and shape of the care module substrate 12, it is not easy to form, on one surface of the care module substrate 12, the power line and the signal transmission line of the care light source 13, and the power line and the signal transmission line of the first sensor part 14 and there is a concern that the performance of the optical outputting device may be deteriorated due to interference between the lines.

Therefore, according to an embodiment of the present disclosure, a circuit (power line and signal transmission line) related to the care light source 13 and a circuit (power line and signal transmission line) related to the first sensor part 14 may be formed on different surfaces.

Referring to FIG. 8, a plurality of care light source mounting pins 125*a* in which the plurality of care light sources 13 are mounted and a plurality of care light source lines 125*b* (power lines, signal transmission lines, or the like) for connecting the plurality of care light source mounting pins 125*a* to terminals of the second substrate fastening portion 123 may be formed on the front surface 12*a* of the care module substrate 12. In addition, a first sensor part mounting pin 127*a* on which components of the first sensor part 14 are mounted may be formed on a front surface 12*a* of the care module substrate 12.

On the other hand, referring to FIG. 9, a plurality of first sensor part lines 127*b* (power lines and signal transmission lines, or the like) for connecting the first sensor part mounting pin 127*a* to a terminal of the second board fastening portion 123 may be formed on a rear surface 12*b* of the care module board 12.

Meanwhile, a terminal mounted in a slot of the sub-board 201 may be formed on the front surface 123*a* and the rear surface 123*b* of the second substrate fastening portion 123. As the terminal is mounted in the slot, the care light source 13 and the first sensor part 14 may be connected to the controller 350 of the user operation device 3 through the interface module 21.

FIG. 10 is an enlarged view of a first sensor part provided in the care module.

Referring to FIG. 10, the first sensor part 14 may include a proximity sensor 141, an RGB LED 142, and color sensors 143*a* and 143*b*. The color sensors 143*a* and 143*b* may include a photodiode for collecting reflected light from which white light emitted from the RGB LED 142 is reflected by the skin.

Referring to (a) of FIG. 10, an inner partition wall 144 may be formed between the components 141, 142, 143*a* and 143*b* of the first sensor part 14. The inner partition wall 144 is formed to have a predetermined height forward from the care module substrate 12, so that interference between the components 141, 142, 143*a*, and 143*b* can be prevented. In addition, the inner partition wall 144 may prevent the white light emitted from the RGB LED 142 from being directly collected by the color sensors 143*a* and 143*b*, thereby making it possible to more accurately detect a skin tone using the color sensors 143*a* and 143*b*.

On the other hand, since the first sensor part 14, in particular, the color sensors 143*a* and 143*b* need to detect the skin tone using the reflected light from which white light is reflected by the skin, it is necessary to prevent the red light of the care light source 13 or external light of various colors from being reflected by the skin and collected by the photodiode.

To this end, as shown in (b) of FIG. 10, outer partition walls 145*a* and 145*b* are formed between the first sensor part 14 and the care light source 13, making it possible to prevent red light emitted from the care light source 13 from being collected by the color sensors 143*a* and 143*b*. The outer partition walls 145*a* and 145*b* may be formed to have a predetermined height forward from the care module substrate 12 like the inner partition wall 144.

FIG. 11 is a diagram showing a care module and a moisture/humidity sensor module provided in a care body, and an interface module provided in a length adjustment part.

Referring to FIG. 11, the care module and the moisture/humidity sensor module may be provided in the care body 1, and the interface module 21 may be provided in the length adjustment part 2.

As described above with reference to FIGS. 2 to 9, the care module substrate 21 of the care module may be connected to the sub-board 201 through the second substrate fastening portion 123. The interface module 21 and the sensor controller 32 may be provided on the sub-board 201. Specifically, a first slot 212 may be formed in the sub-board 201, and a terminal 123*c* corresponding to the first slot 212 may be formed at an end of the second substrate fastening portion 123. The care module may be connected to the interface module 21 and the sensor controller 32 by mounting the terminal in the first slot 212.

The moisture/humidity sensor module may include a moisture/humidity sensor 151 (see FIG. 12) and a sensor substrate 152 having a mounting pin 151*a* in which the moisture/humidity sensor 151 is mounted.

For example, the mounting pin 151*a* may be formed at one end of the sensor substrate 152 and the terminal corresponding to the second slot 214 of the sub-board 201 may be formed at the other end. The other end may be exposed to the outside through the inner frame 162, like the end of the second substrate fastening portion 123 of the care module. The moisture/humidity sensor module may be connected to the sensor controller 32 provided in the sub-board 201 by mounting the terminal in the second slot 214.

Meanwhile, the sub-board 201 may be provided with a cable connection slot (or terminal) 216 to which a cable 4 connected to the user operation device 3 is connected. For example, the cable connection slot 216 may be formed in the upper portion of the sub-board 201, and a portion of the cable 4 adjacent to the cable connection slot 216 may be formed to be bent in a "L" shape. Accordingly, it is possible to prevent the user's inconvenience or discomfort when the cable 4 contacts the user's face or skin.

FIG. 12 is a block diagram illustrating a control configuration of an light outputting device for skincare according to an embodiment of the present disclosure.

Referring to FIG. 12, a care body 1 may include at least one care light source 13, a proximity sensor 141, a color sensor 143, and a moisture/humidity sensor 151.

Each of the at least one care light source 13 may include a RED LED 132 that outputs red light, and an IR LED 134 that outputs infrared light.

The RED LED 132 may emit red light having a wavelength of about 630 nm to 670 nm. Red light stimulates the activity of skin cells and may be effective in improvements in wrinkles, elasticity, and skin tone. The IR LED 134 may emit infrared light of about 780 nm to 1 mm wavelength (precisely about 850 nm). The infrared light provides heat to the user's skin, thereby maximizing a skin improvement effect by the RED LED, and providing additional effects such as relieving fatigue through muscle relaxation.

The controller 350 of the user operation device 3 may provide a skincare function by controlling the care light source 13 based on the operation mode of the light outputting device. The controller 350 may turn on only the RED LED 132, only the IR LED 134, or turn on the RED LED 132 and the IR LED 134 together according to the operation mode.

As the light outputting device is worn by a user, the proximity sensor 141 may detect the proximity of a part of the user's body (e.g., a neck) and transmit a detection signal based on the detection result to the user operation device 3.

For example, when the detection signal is not received, the controller 350 may control the care light source 13 so as not to output light even when the operation mode of the light outputting device is set. The controller 350 may control the care light source 13 to output light when the detection signal is received. That is, the controller 350 may prevent unnecessary power consumption by controlling the light outputting device not to output light when the light outputting device is not worn.

The color sensor 143 may include the color sensors 143a and 143b described above in FIG. 10 and the like. The color sensor 143 may obtain skin color (skin tone) information of a user wearing the light outputting device. Meanwhile, in order for the color sensor 143 to effectively obtain the skin color information of the user, the care body 1 may include an RGB LED 142 that is turned on when the color sensor 143 is operated. The RGB LED 142 outputs white light when the color sensor 143 is operated, so that a photodiode included in the color sensor 143 may more accurately obtain the skin color information.

The moisture/humidity sensor 151 may sense a moisture state of the user's skin and provide a sensing value to the controller 350. The controller 350 may detect the user's skin condition based on the sensing value, and control a driving time or brightness of the care light source 13 according to the detected skin condition.

Meanwhile, an interface module 21 and a sensor controller 32 may be provided in the length adjustment part 2.

The interface module 21 may provide interface among the care module and the moisture/humidity sensor module in the care body 1, the sensor controller 32 in the length adjustment part 2, and the controller 350 of the user operation device 3. For example, the interface module 21 may support an interface according to an I2C (Inter-Integrated Circuit) protocol, but is not limited thereto. In addition, the interface module 21 may include a plurality of slots 212, 214, 216 for electrical connection among the care body 1, the length adjustment part 2, and components in the user operation device 3.

The sensor controller 32 may control operations of the proximity sensor 141, the color sensor 143, the RGB LED 142, and the moisture/humidity sensor 151 provided in the care body 1 according to the control of the controller 350.

For example, when an operation mode of the light outputting device is set, the controller 350 may transmit a control signal to the sensor controller 32 to activate the proximity sensor 141 to detect whether the light outputting device is worn by a user. The sensor controller 32 may activate the proximity sensor 141 in response to the control signal, and transmit a detection signal to the controller 350 when the detection signal is received from the proximity sensor 141.

Meanwhile, when the operation mode of the light outputting device is an automatic mode or a skin tone measurement mode, the controller 350 may transmit a control signal to the sensor controller 32 to activate the color sensor 143 and the RGB LED 142. The sensor controller 32 may activate the color sensor 143 and the RGB LED 142 in response to the control signal and transmit a sensing value received from the color sensor 143 to the controller 350.

In addition, the controller 350 may transmit a control signal to the sensor controller 32 to activate the moisture/humidity sensor 151 to monitor the user's skin condition while the operation mode of the light outputting device is set or light is output from the care light source 13. The sensor controller 32 may activate the moisture/humidity sensor 151 in response to the control signal and transmit a sensing value received from the the moisture/humidity sensor 151 to the controller 350.

The user operation device 3 may include a communication interface 310, an input interface 320, a state output interface 330, a memory 340, a controller 350, and a power supply 360.

The communication interface 310 may include at least one communication module for connecting the light outputting device to a user's mobile terminal (smart phone, tablet PC, or the like) or a server. For example, the at least one communication module may support a short-range wireless communication method such as Bluetooth or a wireless Internet method such as Wi-Fi.

For example, the controller 350 may transmit operation or state information of the light outputting device to the user's mobile terminal through the communication interface 310. In addition, the controller 350 may transmit skin color information or skin condition information of the user to the user's mobile terminal through the communication interface 310. The skin color information and skin condition information may be information obtained based on sensing values of the color sensor 143 and the moisture/humidity sensor 151.

The input interface 320 may receive an input related to power on/off of the light outputting device, settings of an operation mode, and the like from a user. For example, the input interface 320 may include at least one button.

The state output interface 330 may output information on a power state, an operation mode, a battery state, or the like of the light outputting device. For example, the state output interface 330 may include at least one light source 332 and a speaker 334 that outputs the information in an acoustic form.

The memory 340 may include control data for controlling components included in the light outputting device or setting data of care light sources according to each of a plurality of operation modes. In addition, the memory 340 may store data or algorithms for generating skin color information from the sensing value provided from the color sensor 143, and data or algorithms for generating the skin condition information(moisture amount or the like) of the user from the sensing value provided from the moisture/humidity sensor 151.

The memory 340 may be understood as a concept encompassing at least one volatile memory (such as RAM) and at least one nonvolatile memory (such as ROM and Flash memory).

The controller 350 may control the overall operation of the light outputting device. The controller 350 may include at least one processor (or controller). Further, the controller 350 may include at least one CPU, an application processor (AP), a microcomputer, an integrated circuit (IC), an application specific integrated circuit (ASIC), or the like as hardware components.

For example, the controller 350 may include a processor (main processor) 352, a care light source driver 354, an amplifier IC 356, a charger IC 358, and the like.

The processor 352 may correspond to a main processor that controls the overall operation of the light outputting device. For example, the processor 352 may set an operation mode of the light outputting device based on an input received through the input interface 320, and control components included in the light outputting device according to the set operation mode. In addition, the processor 352 may also control the operations of the other components 354, 356, and 358 included in the controller 350.

The care light source driver 354 may control on/off of the care light source 13 provided in the care body 1. The amplifier IC 356 may control sound output of a speaker 334 included in the output interface 330, and the charger IC 358 may control the charge or supply of power of the battery 362 of the power supply 360.

The power supply 360 may provide power required for the operation of the light outputting device to each of the components. For example, the power supply 360 may include the battery 362. The power supply 360 includes a terminal for connection with an external power supply source, and may charge the battery 362 with power supplied from the outside through the terminal.

The above-disclosed subject matter is to be considered illustrative, and not restrictive, and the appended claims are intended to cover all such modifications, enhancements, and other embodiments, which fall within the true spirit and scope of the present invention.

Thus, the embodiment of the present invention is to be considered illustrative, and not restrictive, and the technical spirit of the present invention is not limited to the foregoing embodiment.

Therefore, the scope of the present invention is defined not by the detailed description of the invention but by the appended claims, and all differences within the scope will be construed as being included in the present invention.

The invention claimed is:

1. A light outputting device for skin care, comprising:
a care substrate including one or more light generating elements mounted on the care substrate;
a housing configured to surround the care substrate;
a care body including the care substrate and the housing; and
a length adjuster connected to the care body, the length adjuster comprising two bands,
wherein a size of an overlapping area of the two bands is adjusted by a user,
wherein the housing and the care substrate have a first curvature in a first direction and a second curvature in a second direction crossing the first direction,
wherein the housing includes silicon,
wherein the care substrate includes at least one of polyimide (PI), polyester (PET), or glass epoxy (GE),
wherein the housing includes:
a first inner housing being transparent or opaque,
a second inner housing being transparent, and
an outer housing surrounding the first inner housing and the second inner housing,
wherein the care substrate is disposed between the first inner housing and the second inner housing,
wherein the first inner housing includes stainless steel, and
wherein a double sided adhesive (DSA) layer is disposed between the first inner housing and the care substrate to bond the first inner housing with the care substrate.

2. The light outputting device of claim 1, wherein the first curvature in the first direction and the second curvature in the second direction are arranged in opposite directions from each other with respect to the care substrate.

3. The light outputting device of claim 2, wherein the one or more light generating elements are mounted on an interior surface of the care substrate.

4. The light outputting device of claim 1, wherein the care substrate includes:
a substrate body extending along the first direction; and
a plurality of branch substrates extending in the second direction respectively from a plurality of positions in the substrate body.

5. The light outputting device of claim 4, wherein a plurality of light generating elements are mounted on one side of the substrate body and the plurality of branch substrates, and the plurality of light generating elements are spaced apart from each other.

6. The light outputting device of claim 1, wherein each of the one or more light generating elements includes:
a red light emitting diode (LED) configured to emit red light; and
an infrared (IR) LED configured to emit infrared light.

7. The light outputting device of claim 1, wherein the care body further includes:
a first sensor part including a proximity sensor configured to detect that the user is wearing the light outputting device, and a color sensor configured to detect skin color information of the user; and
a second sensor part including a moisture/humidity sensor configured to detect a skin condition of the user.

8. The light outputting device of claim 7, wherein the first sensor part is disposed on the care substrate, and
wherein the second sensor part is disposed on a sensor substrate spaced apart from the care substrate.

9. The light outputting device of claim 8, further comprising:
a first circuit disposed on the care substrate, the first circuit corresponding to the one or more light generating elements; and
a second circuit disposed on the care substrate, the second circuit corresponding to the first sensor part,
wherein the first circuit and the second circuit are disposed on different surfaces of the care substrate.

10. The light outputting device of claim 8, further comprising:
a partition wall disposed between the first sensor part and at least one of the one or more light generating elements.

11. A light outputting device for skin care, comprising:
a care substrate including one or more light generating elements mounted on the care substrate;
a housing configured to surround the care substrate;
a care body including the care substrate and the housing;
a length adjuster connected to the care body, the length adjuster comprising two bands;
an interface part disposed inside the length adjuster; and
a user operation device connected to the interface part,
wherein a size of an overlapping area of the two bands is adjusted by a user,
wherein the housing and the care substrate have a first curvature in a first direction and a second curvature in a second direction crossing the first direction, and
wherein the care substrate includes a terminal disposed at one end of the care substrate and coupled to a slot of the interface part.

12. The light outputting device of claim 11, wherein the user operation device includes:
a controller configured to control an on/off state of the one or more light generating elements; and
a battery configured to supply power to the care substrate.

* * * * *